United States Patent [19]

Levy

[11] Patent Number: 5,273,713
[45] Date of Patent: Dec. 28, 1993

[54] WATER PURIFICATION AND STERILIZATION PROCESS

[75] Inventor: Guy Levy, Tustin, Calif.

[73] Assignee: Laser Medical Technology, Inc., San Clemente, Calif.

[21] Appl. No.: 901,961

[22] Filed: Jun. 22, 1992

Related U.S. Application Data

[60] Continuation-in-part of Ser. No. 784,976. Oct. 30, 1991, which is a division of Ser. No. 615,789. Nov. 20, 1990, Pat. No. 5,092,773, which is a continuation-in-part of Ser. No. 299,472. Jan. 18, 1989, Pat. No. 5,020,995, and a continuation-in-part of Ser. No. 351,203. May 15, 1989, Pat. No. 5,194,005, which is a continuation-in-part of Ser. No. 335,245, Apr. 10, 1989, abandoned.

[51] Int. Cl.$^5$ .................. A61L 2/00; B08B 17/00; C02F 3/00
[52] U.S. Cl. .................. 422/22; 422/6; 422/23; 210/610; 210/748; 210/749; 435/34; 435/39
[58] Field of Search .................. 422/1, 2, 6, 14, 22, 422/23; 210/610, 739, 748, 749; 433/79, 215, 216, 224, 226; 606/2, 3, 10, 15, 16; 435/34, 36, 37, 38, 39

[56] References Cited

U.S. PATENT DOCUMENTS

| 3,649,493 | 3/1972 | Meiners et al. | 422/22 |
| 3,659,096 | 4/1972 | Kompanek | 422/22 |
| 4,042,325 | 8/1977 | Tensmeyer | 422/22 |
| 4,587,213 | 5/1986 | Malecki | 435/39 |
| 4,692,407 | 9/1987 | Jordan et al. | 435/36 |

Primary Examiner—Robert J. Warden
Assistant Examiner—Christopher Y. Kim
Attorney, Agent, or Firm—Spensley Horn Jubas & Lubitz

[57] ABSTRACT

A method of eliminating bacteria from water without resort to chemicals. The method is carried out by: mixing into the water a dye which stains bacteria contained in the water; and irradiating the water containing the dye with radiation at a wavelength which is absorbed more highly by the dye than by water and at a radiation power density sufficient to vaporize at least a significant proportion of the dye and the bacteria stained by the dye.

10 Claims, No Drawings

WATER PURIFICATION AND STERILIZATION PROCESS

CROSS REFERENCE TO RELATED APPLICATIONS

This is a Continuation-In-Part of application Ser. No. 07/784,976 filed Oct. 30, 1991, which is a division of application Ser. No. 07/615,789 filed Nov. 20, 1990, now U.S. Pat. No. 5,092,773, itself a Continuation-In-Part of application Ser. No. 07/299,472 filed Jan. 18, 1989, now U.S. Pat. No. 5,020,995, and application Ser. No. 07/351,203 filed May 15, 1989 now U.S. Pat. No. 5,194,005, a Continuation-In-Part of application Ser. No. 07/335,245, filed Apr. 10, 1989 now abandoned. These applications are incorporated herein by reference.

BACKGROUND OF THE INVENTION

The present invention relates to the purification and sterilization of water.

Since very few sources of naturally pure drinking water exist, it is the general practice in industrialized countries to subject the available water to chemical purification processes in order to make it suitable for drinking. The most common purification process consists of the addition of a suitable proportion of chlorine to the water supply. Other processes have been explored, but have not achieved any widespread acceptance.

While purification of water by the addition of chlorine appears to be recognized as an acceptable practice, the addition of chlorine represents a cost for obtaining purified water and chlorine represents a chemical additive which could have long term side effects that have not as yet been identified.

In addition to purification of water, sterile water is required for a variety of purposes, particularly in the medical and scientific fields. In order to produce sterile water, it is necessary to destroy all bacteria therein, generally by the application of heat or by chemical additives. The processes employed for producing sterile water are generally too costly to be applied to the drinking water supply for a community.

SUMMARY OF THE INVENTION

It is an object of the present invention to purify or sterilize water in a manner which does not require any chemical additive and which can be applied to large quantities of water in an economical manner.

Another object of the invention is to achieve water purification or sterilization by acting selectively on bacteria contained in the water supply.

Yet another object of the invention is to effect water purification or sterilization by the application of energy in the form of radiation having selected wavelengths.

The above and other objects are achieved, according to the present invention, by a method of eliminating bacteria from water, which method includes mixing into the water a dye which stains bacteria contained in the water; and irradiating the water containing the dye with radiation at a wavelength which is absorbed more highly by the dye than by water and at a radiation power density sufficient to vaporize at least a significant proportion of the dye and the bacteria stained by the dye.

DESCRIPTION OF THE PREFERRED EMBODIMENTS

The invention is based essentially on the realization that there are radiation sources, such as specific types of lasers, which produce radiation at a wavelength which is absorbed more highly by certain materials, including certain dyes, than by pure water and that such radiation can be absorbed by certain dyes which have the ability to stain bacteria. Therefore, if bacteria are stained with such a dye, and radiation at an appropriate wavelength is applied thereto, the energy contained in the radiation will be selectively absorbed by the stain. If the power density of the radiation is at a sufficient level, the energy absorbed by the dye will be sufficient to vaporize both the dye and the bacteria stained thereby. The resulting vaporized material will then escape into the atmosphere in a nontoxic, nonpolluting form.

The dye employed will be selected on the basis of cost, its affinity to the bacteria present in the water, and the efficiency with which it absorbs the radiation employed. A preferred dye material is Nigrosin. Other dyes which may be used to stain bacteria found in water may include methylene blue, dye agaroses, trypan blue, or naphthol blue black. Nigrosin will stain bacteria black. These dyes can be used to stain, among others, staphylococcus, streptococcus, veillonella flora, and bacteroides melanogenicus.

It presently appears that, depending on the bacteria count in the water body, the quantity of dye required is between 0.01% and 5%, by weight of the water, and preferably in the range of 0.1-0.5%, by weight. The composition of the water subsequent to treatment will not be affected by the introduction of a large quantity of dye since, as noted above, substantially all of the dye should be vaporized by the radiation. However, the addition of more dye than required to stain the required percentage of the available bacteria will add to the cost of the process.

After dye has been added to the water and allowed to stain the bacteria present therein, radiation having a selected wavelength, or range of wavelengths, and a selected power density, is delivered to the water in such a manner that each unit of volume of the water receives a sufficient quantity of radiation power for a sufficient time to assure vaporization of all, or substantially all, of the dye present in the water.

Preferably, the radiation is laser radiation at a specific wavelength. Lasers which produce radiation at a wavelength which is absorbed more highly by particular dyes than by water include Nd:YAG, argon and holmium lasers. However, other lasers producing radiation having this selective characteristic may be employed. Moreover, it may be found appropriate to utilize other light sources which, although they produce radiation having a range of wavelengths, also exhibit the characteristic of being absorbed more highly by a particular dye than by water. To the extent that the radiation is not absorbed by water, its energy can delivered to the selected dye.

The selection of a light source will further depend on the energy absorbing characteristics of the selected dye and the input power level which must be supplied to each radiation source to create the radiation power density needed to vaporize the selected dye. All other considerations being equal, the selection of a dye and a radiation source will be based primarily on economic considerations including: the cost of the radiation source and its useful life; the cost of the dye; and the amount of external power which must be supplied to the radiation source to vaporize the dye and the bacteria which it has stained per unit volume of water.

In order to carry out the method according to the invention on a continuous basis, the water can be caused to flow through a channel dimensioned to promote, firstly, thorough mixing of dye in the water and, secondly, uniform exposure of the water to the radiation.

As regards mixing of the dye, this could be facilitated by adding the dye at a location where a certain level of turbulence is being induced in the water.

For application of the laser radiation, a wide variety of options is available. Since the radiation employed may be at a wavelength to which the water is substantially transparent, the water may be channelled to have a substantial dimension in the direction of propagation of the radiation. Typically, the radiation will be propagated downwardly from above, so that the relevant dimension will be the depth of the water. However, as the depth of the body of water decreases, the power density at the surface of the body of water can be reduced.

In addition, when the water being treated is flowing past the radiation source, the power density at the surface of the water must be proportional to the water velocity.

Finally, as regards the area of impingement of the radiation on the surface of the water body, in the case of a flowing stream of the water, the area of impingement should extend across the entire width of the stream and should extend in the direction of the length of the stream by an amount which is determined on the basis of the power content of the applied radiation, the quantity of energy which must be supplied to each unit volume of the water and the rate at which that energy must be supplied to the water. The power density of the applied radiation must be selected on the basis of the quantity of energy to be supplied to each unit volume of the stream, the rate at which that energy must be delivered, the depth of the stream, and the length of time during which each elemental volume of water is exposed to the radiation.

In any event, the desired combination of parameters can be selected on the basis of principles known in the art, particularly as they relate to the quantity of energy at the selected wavelength and the rate at which that energy must be supplied, to vaporize the selected dye and bacteria stained thereby, as well as attainable values for the area of coverage of the selected radiation and the radiation power density, and the rate at which water must be treated.

The method according to the present invention makes possible the purification of water for drinking purposes without the use of any chemical additive which will be present in the water after treatment. Moreover, since the method according to the invention has the effect of removing bacteria from the water, it can also be employed to produce sterile water for medical and scientific uses. In this case, however, the level of radiation energy needed to eliminate all bacterial must be carefully determined and, as a matter of precaution, the intensity of the radiation should be selected to be in excess of that determined to be necessary to vaporize all bacteria. Similarly, the quantity of dye employed should be in excess of that required to stain all bacteria present in the water.

The radiation employed in the practice of the present invention may be in continuous wave form. While the radiation may also be in the form of pulses, there is no reason to believe, at the present time, that to achieve the results contemplated by the present invention, pulsed radiation would offer any benefits.

Investigations conducted to date indicate that the desired purification could be achieved by operating one of the lasers mentioned above to deliver power such that each cubic centimeter of water receives 200 watts during a period of one second. Depending on the type of laser and type and quantity of dye employed, the power per unit volume required to achieve the desired result could vary between 20 and 2000 watts/cc. In addition, appropriate alterations could be made in the level of power per unit volume in association with a variation in the irradiation time per unit volume.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A method of eliminating bacteria from water comprising:
   mixing into water a dye which stains bacteria contained in the water; and
   irradiating the water containing the dye with radiation at a wavelength which is absorbed more highly by the dye than by water and at a radiation power density sufficient to vaporize at least a significant proportion of the dye and the bacteria stained by the dye.

2. A method as defined in claim 1 wherein said step of irradiating is carried out at an irradiation location while the water flows continuously past that location.

3. A method as defined in claim 2 wherein the radiation is supplied by a laser.

4. A method as defined in claim 3 wherein said step of mixing is performed before the water passes the location where said irradiating step is performed.

5. A method as defined in claim 1 wherein said step of mixing is performed by introducing into the water a quantity of dye in excess of that required to stain all of the bacteria present in the water, and said step of irradiating is carried out to vaporize substantially all of the dye and the bacteria stained by the dye.

6. A method as defined in claim 1 wherein said step of mixing is carried out by introducing between 0.01% and 5% of dye, by weight of water.

7. A method as defined in claim 6 wherein said step of mixing is carried out by introducing between 0.1% and 0.5% of dye, by weight of water.

8. A method as defined in claim 7 wherein the dye is at least one substance selected from among nigrosin, methylene blue, dye agaroses, trypan blue, and naphthol blue black.

9. A method as defined in claim 6 wherein the dye is at least one substance selected from among nigrosin, methylene blue, dye agaroses, trypan blue, and naphthol blue black.

10. A method as defined in claim 1 wherein the dye is at least one substance selected from among nigrosin, methylene blue, dye agaroses, trypan blue, and naphthol blue black.

* * * * *